United States Patent
Lavallee et al.

(10) Patent No.: US 12,295,670 B2
(45) Date of Patent: May 13, 2025

(54) METHOD AND SYSTEM FOR DETERMINING AN OPTIMAL POSITION OF A SURGICAL INSTRUMENT RELATIVE TO A PATIENT'S BONE TRACKER

(71) Applicant: ECENTIAL ROBOTICS, Gieres (FR)

(72) Inventors: Stéphane Lavallee, St Martin d'Uriage (FR); David Armand, Saint Egreve (FR)

(73) Assignee: ECENTIAL ROBOTICS, Gieres (FR)

( * ) Notice: Subject to any disclaimer, the term of this patent is extended or adjusted under 35 U.S.C. 154(b) by 367 days.

(21) Appl. No.: 17/770,687

(22) PCT Filed: Nov. 12, 2020

(86) PCT No.: PCT/EP2020/081869
§ 371 (c)(1),
(2) Date: Apr. 21, 2022

(87) PCT Pub. No.: WO2021/094431
PCT Pub. Date: May 20, 2021

(65) Prior Publication Data
US 2022/0370152 A1    Nov. 24, 2022

(30) Foreign Application Priority Data

Nov. 12, 2019  (EP) ..................................... 19306464

(51) Int. Cl.
*A61B 34/20*    (2016.01)
*A61B 6/03*    (2006.01)
(Continued)

(52) U.S. Cl.
CPC .............. *A61B 34/20* (2016.02); *A61B 6/032* (2013.01); *A61B 6/4085* (2013.01); *A61B 6/583* (2013.01);
(Continued)

(58) Field of Classification Search
CPC ......... A61B 34/10; A61B 34/20; A61B 34/30; A61B 6/032; A61B 2090/3764;
(Continued)

(56) References Cited

U.S. PATENT DOCUMENTS

2002/0183610 A1    12/2002  Foley et al.
2008/0269588 A1*  10/2008  Csavoy .................. A61B 5/704
                                                                    600/407
(Continued)

FOREIGN PATENT DOCUMENTS

| EP | 3326564 A1 | 5/2018 |
|---|---|---|
| EP | 3398551 A1 | 11/2018 |
| WO | 2017064290 A1 | 4/2017 |

OTHER PUBLICATIONS

Breakaway Imaging Receives FDA ok for Its O-arm Imaging System; News release published online on May 18, 2005 (Year: 2005).*

(Continued)

*Primary Examiner* — Chao Sheng
(74) *Attorney, Agent, or Firm* — Thomas | Horstemeyer, LLP

(57) ABSTRACT

The invention relates to a system for determining an optimal position of a surgical instrument relative to a patient's bone tracker, the system comprising:—a medical imaging system configured to acquire at least one cone beam computed tomography intraoperative image of the patient;—a localization device;—a computer configured to receive images from the medical imaging system and localization data from the localization device and to implement the following method: the method comprising: •(a) receiving at least one preoperative 2D X-ray image of the bone while the patient is in a position of interest; •(b) acquiring an intraoperative 3D medical image of the bone by cone beam computed tomography while the patient is in an operative position (Continued)

different from the position of interest, the 3D image being registered with the coordinate system of the bone tracker; •(c) registering the intraoperative 3D medical image onto the at least one preoperative 2D X-ray image, so as to obtain a registered 3D image representing the bone in the position of interest; •(d) planning a surgical procedure on the registered 3D medical image taking into account said position of interest; •(e) determining an optimal position of the surgical instrument relative to the patient's bone tracker for implementing said planned surgical procedure.

21 Claims, 6 Drawing Sheets

(51) Int. Cl.
*A61B 6/40* (2024.01)
*A61B 6/58* (2024.01)
*A61B 34/10* (2016.01)
*A61B 34/30* (2016.01)
*G06T 7/33* (2017.01)
*G06T 7/73* (2017.01)
*A61B 90/00* (2016.01)

(52) U.S. Cl.
CPC .............. *A61B 34/10* (2016.02); *A61B 34/30* (2016.02); *G06T 7/337* (2017.01); *G06T 7/73* (2017.01); *A61B 2034/102* (2016.02); *A61B 2090/3764* (2016.02); *A61B 2090/3966* (2016.02); *A61B 2090/3983* (2016.02); *G06T 2200/04* (2013.01); *G06T 2207/10081* (2013.01); *G06T 2207/10116* (2013.01); *G06T 2207/30008* (2013.01)

(58) Field of Classification Search
CPC .... A61B 2090/3966; A61B 2090/3983; A61B 6/4085; A61B 6/583; A61B 2034/102; G06T 7/73; G06T 7/337; G06T 2200/04; G06T 2207/10081; G06T 2207/10116; G06T 6/30008
See application file for complete search history.

(56) References Cited

U.S. PATENT DOCUMENTS

2014/0334709 A1* 11/2014 Siewerdsen .............. G06T 7/32
                                                           382/132
2015/0227679 A1   8/2015 Kamer et al.
2018/0036015 A1* 2/2018 Bonutti .............. A61B 17/1717
2018/0279913 A1* 10/2018 Frasier .................. A61B 6/545

OTHER PUBLICATIONS

Ali Hamadeh et al.—"Automated 3-Dimensional Computed Tomographic and Fluoroscopic Image Registration"—pp. 11-19—(1998).
Ali Hamadeh et al.—"Kinematic study of lumbar spine using functional radiographies and 3D/2D registration"—CVRMed 1997, MRCAS 1997—Part of the Lecture Notes in Computer Science book series (LNCS, vol. 1205).
European Search Report in related EP Application No. 19306464, mailed Apr. 24, 2020.
PCT International Search Report in related PCT Application No. PCT/EP2020/081869, mailed Feb. 5, 2021.

* cited by examiner

METHOD AND SYSTEM FOR DETERMINING AN OPTIMAL POSITION OF A SURGICAL INSTRUMENT RELATIVE TO A PATIENT'S BONE TRACKER

CROSS REFERENCE TO RELATED APPLICATIONS

This application is the 35 U.S.C. § 371 national stage application of PCT Application No. PCT/EP2020/081869 filed Nov. 12, 2020, which application claims the benefit of European No. EP 19306464.9 filed Nov. 12, 2019, both of which are hereby incorporated by reference herein in their entireties.

FIELD OF THE INVENTION

The invention relates to a method and a system for determining an optimal position of a surgical instrument relative to a patient's bone tracker. Said method can in particular be used for navigating a tool and/or an implant in a 3D image during the surgical intervention.

BACKGROUND OF THE INVENTION

When navigation of a surgical tool and/or an implant is to be carried out on a 3D image of a patient's bone, or when said surgical tool and/or implant is carried by a robotic device, the method for performing the surgical procedure may be as follows.

First, a 3D image of the bone is acquired preoperatively, for example using a CT scan. During the acquisition of said 3D image, the patient is typically in a lying position. Said preoperative 3D image is used to plan the surgical intervention.

During the surgical intervention, there exist several methods of registration of pre-operative images with the patient position during surgery. In particular, intraoperative 2D X-ray images of the bone can be acquired for that purpose. The 2D X-ray images can be registered with the 3D preoperative image in view of navigating the tool and/or implant on the 2D X-ray images (fluoronavigation).

In both cases, the 2D and 3D images of the bone are acquired when the patient is lying on the operating table.

Document US 2008/0269588 relates to a method comprising a registration between preoperative and intraoperative images of a patient's cranium, allowing registering a preoperative planning to the patient space during cranial surgery.

However, whether the patient is lying or standing may strongly influence the configuration of the bone. For example, when the bone is the patient's pelvis, the inclination and the anteversion of the acetabulum greatly vary between the lying and the standing position.

Thus, if the surgeon carries out the surgical intervention taking only into account the configuration of the bone in the operative position, the result may not be optimal for the patient in standing position.

It may be possible to take into account the standing position of the patient by acquiring a lateral X-ray image of the patient in order to measure the pelvis tilt, and use the measured value of the tilt to correct the images by one angle, but this procedure is not accurate.

Document EP 3 398 551 relates to a method for preoperatively planning a total ankle replacement that intends to take the standing position of the patient into account. To that end, 2D X-ray images of the patient's leg are acquired while the patient is in standing position, and a 3D CT image of the patient's leg is acquired while the patient is in supine position. The 3D CT image is segmented to generate 3D models of the patient's bones. These 3D models are then registered on the 2D preoperative images, so as to represent the models in the standing position of the patient. The planning may thus be done on said reoriented models.

However, said method suffers from several drawbacks.

First, this method is carried out preoperatively. In order to perform the surgical intervention, the surgeon has to register the preoperative planning performed on hybrid 3D CT and 2D x-ray images with an intra-operative patient position located by a navigation system. Said registration may be made by various techniques (e.g. palpation of a number of points on the bone surface, acquisition of an intraoperative 2D or 3D image and registration of the preoperative planning onto said intraoperative image). In any case, said registration involves at least one additional step in the surgical procedure.

Besides, the acquisition of the preoperative 3D image such as a CT scan, necessary to obtain an image quality adapted to segmentation, is expensive and involves a significant exposure of the patient to X-rays, which is undesirable.

Magnetic resonance imaging (MRI) does not expose the patient to such an irradiation, but the acquisition of a 3D image takes a much longer time than a CT scan, and it is also very expensive and not always accurate in three dimensions.

BRIEF DESCRIPTION OF THE INVENTION

A goal of the invention is to provide a method for determining an optimal position of a surgical instrument relative to at least one patient's bone tracker taking into account a position of interest of the patient that overcomes the above drawbacks.

In particular, a goal of the invention is to minimize the number of steps to carry out the surgical procedure and to minimize the exposure of the patient to X-rays.

In particular, a goal of the invention is to obtain a planning of the surgical procedure that takes into account a position of interest of the patient, without using CT scans, whether preoperatively or intraoperatively.

A first embodiment relates to a method for determining an optimal position of a surgical instrument relative to a tracker attached to a patient's bone using a cone beam computed tomography (CBCT) imaging system and a computer, comprising the following steps:

(a) receiving at least one preoperative 2D X-ray image of the bone while the patient is in a position of interest;

(b) acquiring an intraoperative 3D medical image of the bone by the cone beam computed tomography (CBCT) imaging system while the patient is in an operative position different from the position of interest, the 3D image being registered with the coordinate system of the bone tracker;

(c) registering with the computer the intraoperative 3D medical image onto the at least one preoperative 2D X-ray image, so as to obtain a registered 3D image representing the bone in the position of interest;

(d) planning with the computer a surgical procedure on the registered 3D medical image taking into account said position of interest;

(e) determining with the computer an optimal position of the surgical instrument relative to the patient's bone tracker for implementing said planned surgical procedure.

A second embodiment relates to a method for determining an optimal position of a surgical instrument relative to trackers respectively attached to at least two patient's bone trackers using a cone beam computed tomography (CBCT) imaging system and a computer, comprising the following steps:

(a) receiving at least one preoperative 2D X-ray image of the at least two bones while the patient is in a position of interest;

(b) acquiring at least one intraoperative 3D medical image of each bone by the cone beam computed tomography (CBCT) imaging system while the patient is in an operative position different from the position of interest, each 3D image being registered with the coordinate system of each bone tracker;

(c) performing one of steps c1) and c2) with the computer:
  (c1) determining a region around each bone in the at least one preoperative 2D X-ray image and registering said at least one region onto the intraoperative 3D medical image, so as to obtain a registered region around said bone in the 3D medical image representing said bone in the position of interest;
  (c2) determining a region around each bone in the 3D intraoperative medical image and registering said region onto the at least one preoperative 2D X-ray image, so as to obtain a registered region around said bone in the at least 2D preoperative X-ray image representing said bone in the position of interest;
  (c3) computing with the computer an integrated 3D medical image from the registered regions determined in step (c1) or (c2);

(d) planning with the computer a surgical procedure on the integrated 3D medical image taking into account said position of interest;

(e) determining with the computer an optimal position of the surgical instrument relative to the patient's bone trackers for implementing said planned surgical procedure.

In navigation or surgical robotic devices, it is necessary to use a localization device which locates positions and orientations of trackers that can be attached to bones, surgical instruments, sensors or any other device. Such localization devices may use various technologies, including optical, magnetic, inertial, ultrasonic systems.

In the present text, a bone tracker means a device configured to be rigidly connected to a patient's bone. By "rigid connection" is meant a connection that is not deformable beyond the accuracy required to localize the tracker for the intended surgical application. For example, a rigid connection may be an attachment of the tracker directly to the bone, or to a body part in the vicinity of the bone which is relatively stable with the desired accuracy.

Such a bone tracker comprises at least a base configured for the rigid attachment to the patient's bone and at least one element detectable by the localization device.

The tracker may comprise different elements, that may be reproducibly detachable.

Many navigation or surgical robotic devices use such trackers to assist or guide a surgical intervention optimally.

In the present text, the term "intraoperative" designates a step that is implemented in the operative room, when the patient has been equipped with the bone tracker(s). It is to be noted that the step of attachment of the bone tracker(s) is to be considered as a preliminary step and is excluded from the present invention.

In the present text, a surgical instrument may be a surgical tool (e.g. a burr, a saw, a reamer, a drill . . . ) or an implant (e.g. a hip prosthesis, a pedicular screw, a vertebra cage, a disc prosthesis . . . ). The surgical instrument is equipped with a tracker to be localized with respect to the bone tracker. In some embodiments (e.g. in spine surgery), the surgical instrument may be replaced by a bone tracker itself. The surgical instruments can be navigated manually or guided by passive, haptic or active robotic devices.

By "equipped" is meant in the present text that the tracker is attached directly to the instrument or to another device coupled to the instrument (e.g. an instrument holder, or a device operating the instrument such as a robot), in such a way that the instrument can be localized using said tracker.

Contrary to the methods described above, the method according to the invention benefits from CBCT imaging (Cone Beam Computed Tomography), which is an imaging technique commonly used intraoperatively, in particular with imaging devices having an open C architecture, well known as C-arm. Said technique provides a smaller exposure of the patient to X-rays. Although the quality of a CBCT image is usually lower than the one of a CT image, this is not detrimental to the method since the method does not require any segmentation of the patient's bone(s). CBCT devices that can used during surgery include Surgivisio products, but also O-arm™ (Medtronic), Artis Zeego™ (Siemens), CIOS™ (Ziemens), Loop-X™ (Brainlab), Vario3D™ (Ziehm). The invention principles described below can also be used if a CT imaging device is used instead of CBCT during surgery, preferably a low-dose CT imaging device.

Besides, the method according to the invention is also advantageous in that the planning, which is done intraoperatively, can be directly applied to carry out the surgical procedure. Indeed, the planning is done in a coordinate system attached to the bone tracker. Thus, the global time and number of steps are reduced as compared to a surgical procedure using a planning as described in document EP 3 398 551.

By "position of interest" or "operative position" is meant in the present text a physical configuration that a human body can take. The operative position is the position of the patient during a surgical procedure to treat the bone(s) according to the above-mentioned planning. The position of interest is a position that the body can take during the patient's normal life and activities.

In some embodiments, the position of interest is a standing position of the patient.

In some embodiments, the operative position is a lying position of the patient.

In some embodiments, the at least one preoperative 2D X-ray image received in step (a) is geometrically calibrated, the features of the geometric projection of an imaged object onto the image plane being known.

In some embodiments, at least two 2D X-ray images are received in step (a) and said images are geometrically calibrated (the features of the geometric projection of an imaged object onto each image plane being known) and registered with each other.

In some embodiments, step (d) comprises a step of importing a preoperative planning based on the at least one preoperative 2D X-ray image received in step (a).

In some embodiments, the method comprises acquiring at least two intraoperative 2D X-ray images on which at least one anatomical landmark of the patient is visible and determining a position of said anatomical landmark of the patient from said intraoperative 2D X-ray images.

The method may further include navigating a tool and/or an implant on the registered 3D image.

The method may further include using a robot to position a tool and/or prepare the bone to receive an implant.

In some embodiments, step (e) uses a preoperative planning based on the at least one preoperative 2D X-ray image acquired in step (a).

Another object of the invention is a system for implementing the method described above.

BRIEF DESCRIPTION OF THE DRAWINGS

Further features and advantages of the invention will be apparent from the description that follows, based on the appended drawings, wherein.

DETAILED DESCRIPTION OF EMBODIMENTS OF THE INVENTION

Surgical System

Figure 1:
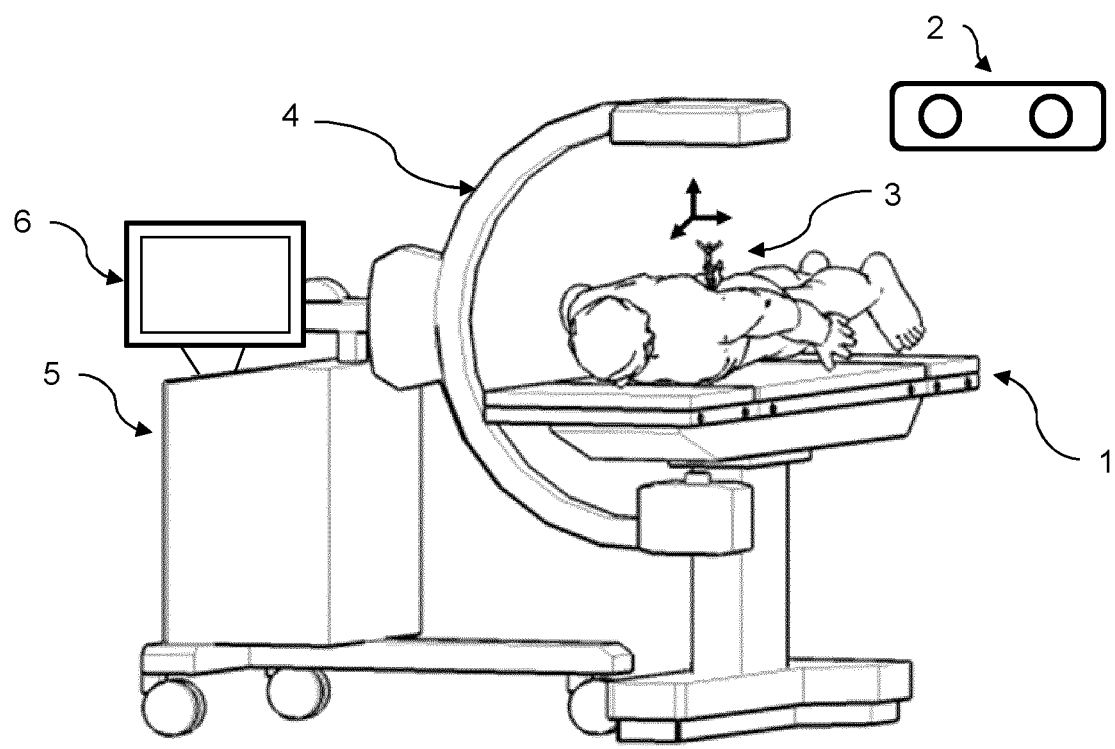
FIG. 1 is a perspective view of a surgical system according to an embodiment of the invention.

FIG. 1 represents a surgical system configured for carrying out the invention.

The system comprises an operating table 1 onto which the patient may lie, e.g. in prone, supine or lateral position.

The system comprises a localization device 2.

The patient is equipped with at least one bone tracker 3 which may be localized in real time by the localization device.

The system further comprises a CBCT imaging system in the form of a C-arm 4. The imaging system comprises at least one X-ray source and at least one X-ray 2D detector. The imaging system is configured to rotate and/or translate relative to the operating table in order to acquire intraoperative 2D and/or 3D images of the patient. The imaging system may be motorized on at least one movement which contributes to generate a 3D acquisition trajectory, i.e. each movement of the system according to a degree of freedom is generated by a respective motor. Each motor is associated to an encoder allowing knowing, at any time, the relative position of the imaging system with respect to a reference position. When a 2D image is acquired, the corresponding position of the imaging system is recorded. Thus, each 2D image is recorded in the referential of the imaging system. The imaging system allows constructing a 3D image from a set of 2D images may be used for reconstruction of a 3D image.

The system further comprises at least one computer 5 configured to receive images from the C-arm and localization data from the localization device and to implement the algorithms described below to perform the method according to the invention.

The system may further comprise a display monitor 6 coupled to the computer and configured to display the registered 3D image along with the planning.

Tracker

The bone tracker comprises a base allowing rigid fixation to a patient's bone.

The fixation may be either direct (e.g. using at least one percutaneous pin, needle, broach or screw implanted into the bone in a minimally invasive way) or indirect (i.e. using attachment means external to the bone, such as an adhesive tape on the skin close to the bone, straps, etc. to immobilize the base with respect to the bone without passing through the patient's skin). According to an embodiment, a deformable material may be interposed between the base and the skin. Said deformable material can be silicon, thermosetting foam, a bag containing microbeads that can be rigidified under vacuum, or an adhesive tape. The material fitting to the body part shape provides some stability to the base relative to the bone, especially in non-flat regions. Adhesion between the material and the skin and the base can be obtained either by adhesive properties of the material or by external means such as straps, adhesive tape surrounding the base. The indirect fixation is particularly adapted when there is only a small thickness of soft tissues between the bone and the base, since this situation is considered to provide sufficient rigidity to prevent any movement of the base relative to the bone. For example, indirect fixation can be used when the bone pertains to a patient's finger, wrist, foot, etc. Such an indirect fixation has the advantage of being non-invasive. If required, direct and indirect fixation can be combined. For example, the base may be linked to the skin via a deformable material that fits to the body part shape and at least one percutaneous pin, broach, needle or screw further secures the base to the bone. If the intervention is performed on several bones, or several bone fragments, it is possible to use multiple bases, one base per bone or bone fragment. In a preferred embodiment, such as a complex articulation of several bones, a deformable material that can become rigid is first used to fix the individual bones or bone fragments together: conventional plaster, thermo-deformable material, poach of micro spheres with vacuum, etc. and the base is then fixed to this deformable material once it is rigid.

The base advantageously has generally a height of less than 20 mm. In this way, the base is very compact and protrudes only to a limited extent from the patient's skin. Thus, it is quite unlikely that the medical staff unintentionally hits the base and thus displaces it relative to the bone during the surgical intervention.

The tracker further comprises at least one localization element rigidly coupled thereto. Said coupling can be permanent (the localization element being integral with the base or irreversibly fixed to the base) or temporary (the localization element being detachable from the base).

According to a preferred embodiment, the localization element can be detached from the base when no tracking is required, thus offering a temporary coupling. This reduces the risk of having the localization element hit by the medical staff and thus causing a displacement of the base relative to the bone. It also saves operating space when the tracker is not needed.

In the case of said temporary coupling, the base and localization element have cooperating fixation means that allow detaching and attaching the localization element in a reproducible way (i.e. always in a same known position and orientation relative to the base).

According to an embodiment, the tracker is an optical tracker (either active or passive). For example, the localization element comprises a plurality of reflective balls having a known relative position.

According to another embodiment, the tracker is an electromagnetic tracker, the localization element being an electromagnetic sensor. An electromagnetic tracker has the advantage of being more compact than an optical tracker. The localization element may be removable or not from the base. For example, the localization element may be embedded in a support which can be attached to the base with reproducible fixation means. In an alternative embodiment, the localization element may be lodged in a recess of the base and thus does not protrude from the base. In a preferred embodiment, the electromagnetic tracker contains inertial sensors that can be used to detect the presence of artefacts.

The invention is not limited to a specific tracking technology and the skilled person can adapt the described embodiments to the selected technology.

A tracker is usually attached to each bone of interest. But it is also possible to extrapolate or interpolate the positions of trackers between non-adjacent bones.

Advantageously, during surgery, a registration phantom may also be rigidly attached to the tracker base. The registration phantom is made of a radiotransparent material and comprises a plurality of radiopaque fiducials having a known shape and size (e.g. balls or pins) arranged in a known position.

When a 2D image is acquired with the imaging system, the radiopaque fiducials are visible in the 2D image. Since the shape, size and arrangement of the radiopaque fiducials is known, the image can be determined in the referential of the calibration phantom and the 3D reconstruction can be carried out based on the position of the radiopaque fiducials in each 2D image. It is also possible to perform a 3D image reconstruction directly without using the fiducials and then to detect the fiducials directly in the reconstructed 3D image.

Since the registration phantom is not required during the whole surgical intervention but only at specific times when registration of the images acquired by the imaging system has to be carried out, the registration phantom is detachable from the base.

To that end, the base and the registration phantom have cooperating fixation means that allow attaching the registration phantom in a reproducible way (i.e. always in a same known position and orientation relative to the base). This allows saving operating space when the phantom is not needed.

The registration phantom may have any shape and size suitable for the intended application. In particular, since the registration phantom is only attached to the base when it is required for image registration, the registration phantom can have a greater size than the base. In this way, it is possible to have the radiopaque balls located at a greater distance from each other and thus improve the accuracy of the registration.

Advantageously, the registration phantom and, if applicable, the localization element, is maintained onto the base using magnetic force thanks to a magnet arranged in the base. Thus, attachment and removal of the registration phantom and, if applicable, the localization element, can be made easily without requiring any tool. This magnetic fixation has also the advantage of being detached automatically if a certain level of force is exerted on the part mounted to the base, which avoids damaging or displacing the relative position and fixation of the base with respect to the bone.

One may refer to document WO 2017/064290 in the name of the Applicant which teaches various embodiments of a modular device comprising a base, a registration phantom and a localization element.

Figure 2:
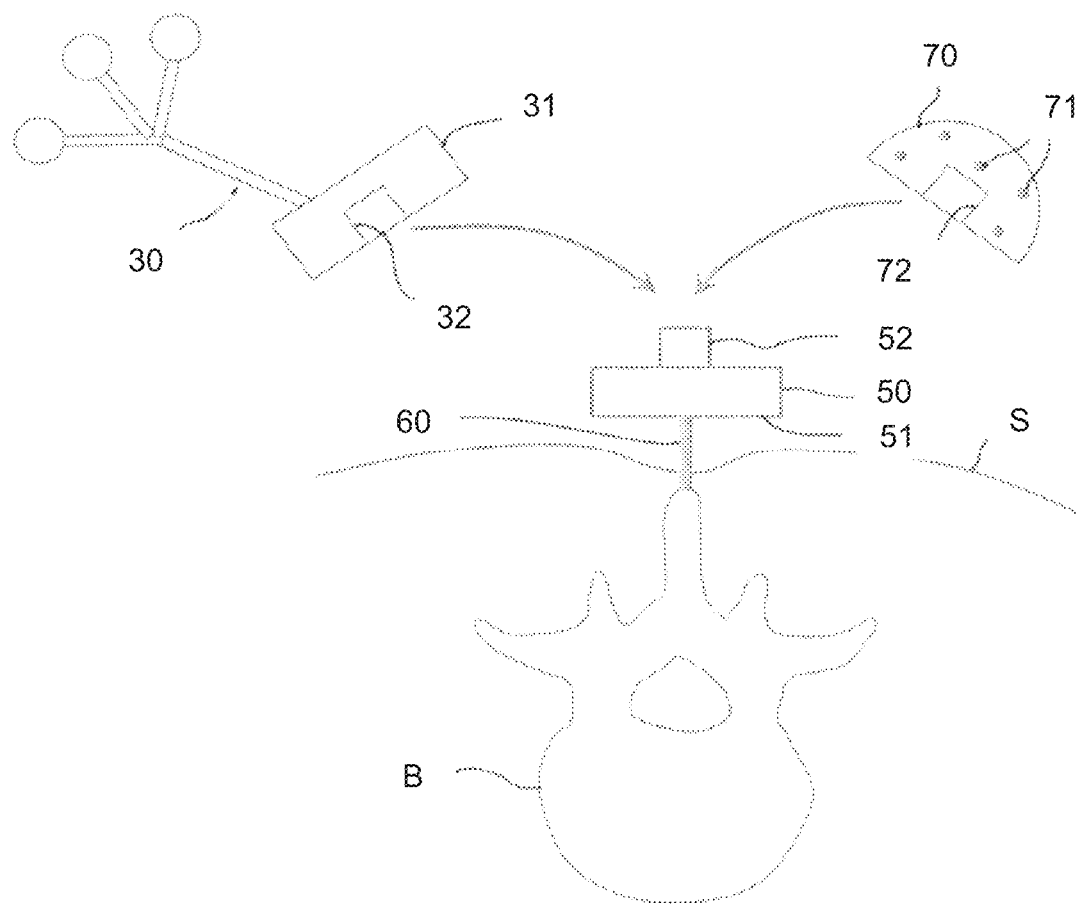
FIG. 2 is a schematic view of a modular device comprising a base, a localization element and a registration phantom that may be used in an embodiment of the invention.

FIG. 2 illustrates a preferred embodiment of such a device in the case of optical tracking technology. The base 50 may be attached to the bone B by a percutaneous pin 60. The base may be in contact with the patient's skin S or may be maintained at a certain distance from the skin. The base comprises a reproducible fixation 52 for both the registration phantom 70 and the localization element 30. In this way, the design of the base is as simple as possible and no space is lost by providing two distinct fixations areas on the base. The localization element 30 comprises an interface 31 with the base provided with a fixation 32 cooperating with the fixation 52 of the base. The registration phantom 70 comprises a plurality of radiopaque fiducials 71 and a fixation 72 cooperating with the fixation 52 of the base. When assembled, the base 50 and localization element 30 together form a bone tracker.

Method

The surgical intervention is intended to operate at least one patient's bone and/or to place an implant into said bone.

Depending on the application, the intervention is carried out on a single bone or to a plurality of bones. In the latter case, the bones may form a joint (e.g. hip or knee) or may belong to a more complex anatomical structure (e.g. spine).

The method according to the invention may be implemented in different manners depending on the application.

Figure 3:
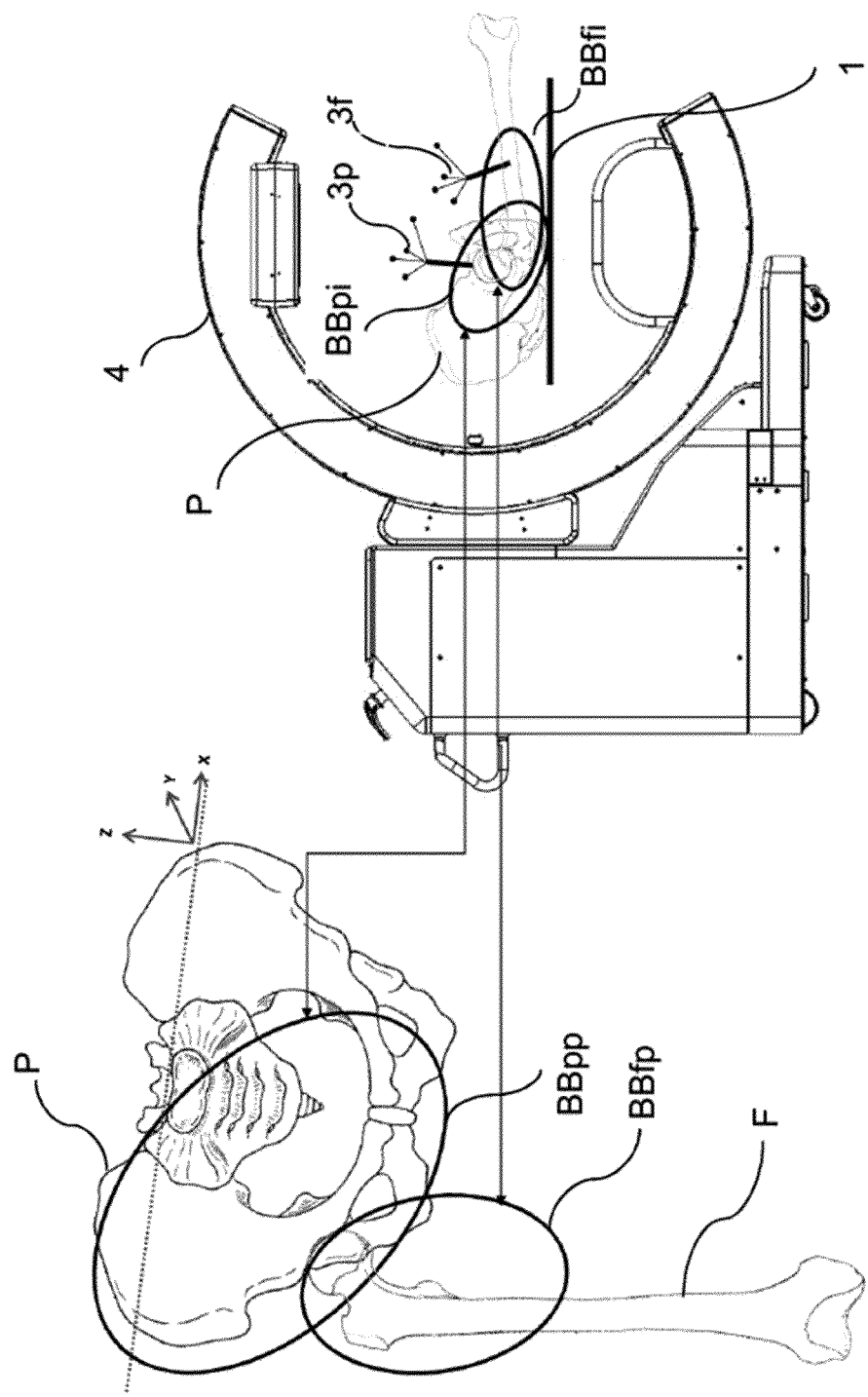
FIG. 3 schematically represents a preoperative image (left) and the intraoperative setting (right) for hip surgery.

FIG. 3 schematically represents a preoperative image (left) and the intraoperative setting (right) for hip surgery. The preoperative image is acquired with the patient in standing position, whereas during the surgical intervention the patient lies in supine position on the operating table 1, the femur and the pelvis being each equipped with a respective tracker 3f, 3p. The relative positions of the pelvis P and femur F are thus different between the preoperative image and the intraoperative image acquired by the C-arm 4. However, as will be explained in more detail below, a registration of at least part of both images will be carried out. This registration, which is represented by the arrows, generally involves bounding boxes BBfp, FFpp that define regions of interest in the preoperative image and/or bounding boxes BBfi, BBpi that define regions of interest in the intraoperative images.

Figure 4:
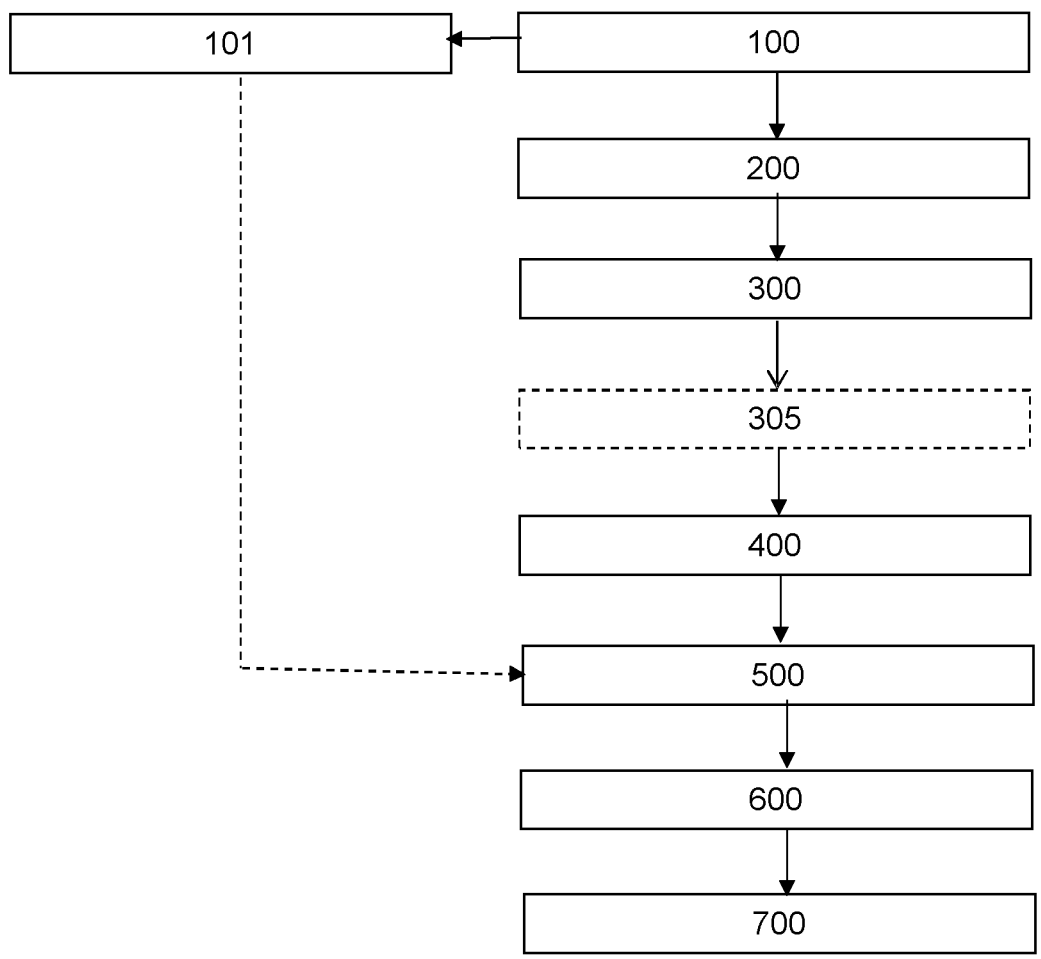
FIG. 4 represents a flow chart of the method according to a first embodiment of the invention.

FIG. 4 is a flow chart of the method according to an embodiment of the invention, which may be applicable in particular when a single bone is to be operated.

In step 100, at least one preoperative 2D X-ray image is received. Said at least one image may have been acquired in another place than the operative site, for example in a radiology centre. The image may be transmitted to the surgical system by any suitable communication means, such as a PACS network.

During the acquisition of said preoperative 2D X-ray image(s), the patient is in a position of interest, i.e. a position that has an impact on the configuration of the bone and on the interaction of the bone with other anatomical structures of the patient.

For example, said position of interest may be a standing position. Indeed, in this position, the lower members of the patient bear the patient's weight and the relative position of the spine, pelvis, and bones of the lower members may be impacted by said weight and by the natural patient's posture.

Each image is geometrically calibrated, i.e. the features of the geometric projection of the imaged object onto the plane of the image are known.

According to an embodiment, only a frontal 2D X-ray image of the patient may be acquired.

According to another embodiment, both a frontal and a lateral 2D X-ray image may be acquired. Said images are then registered with each other, and the registered images are received by the surgical system. For example, said frontal and lateral images may be acquired simultaneously using two X-ray beams by an imaging system provided by EOS Imaging™.

In step 200, the patient is installed in the operating room, on the operating table, and equipped with a bone tracker. As mentioned above, the bone tracker may be attached directly to the bone, or to a body part rigidly connected to the bone, e.g. the patient's skin in particular if soft tissues extending between the skin and the bone are not too thick. The bone tracker defines a coordinate system.

In case the bone tracker is made of several detachable elements, only a part of these elements (in particular, the base) may be attached to the patient at this stage.

Step 200 and the following steps belong to the intraoperative part of the method.

In step 300, a 3D image is acquired by the CBCT imaging system.

To that end, with a modular device as described above, the registration phantom is attached to the base using the reproducible fixation. The motorized imaging system acquires a plurality of 2D X-ray images of the patient in the region of the bone. A 3D reconstruction algorithm is implemented by the computer so as to generate a 3D image which is defined in the referential of the imaging system. 3D reconstruction is known per se and thus will not be described in detail here.

A registration algorithm is implemented by the computer so as to generate the 3D volume in the referential of the registration phantom, based on the known phantom dimensions that are stored in a memory of the computer or that may be downloaded from another system.

Since at least the base of the bone tracker is attached to the patient during the acquisition, the 3D image may be registered to the coordinate system of the bone tracker.

In case only one preoperative 2D X-ray image has been received in step 100, it may be advantageous to acquire anatomical landmarks of the patient in step 305. Step 305 may be carried out before or after step 300. Step 305 involves the acquisition of several 2D X-ray images, so that each anatomical landmark is visible in at least two of said images.

For example, in hip surgery, the Lewinnek plane is a reference plane of the pelvis, which is linked to the balance of the pelvis. Said plane is defined as being the plane containing the left and right anterior superior iliac spine (ASIS) and the pubic symphysis. The coordinates of the Lewinnek plane, in addition to the 2D frontal X-ray image, allow fully defining the orientation of the patient's pelvis in the standing position.

According to another example, in spine surgery, it may be useful to take into account the pelvis tilt, by acquiring anatomical landmarks of the pelvis in addition to 2D X-ray images of the vertebrae.

In step 400, the intraoperative 3D medical image is registered onto the at least one preoperative 2D X-ray image, so as to obtain a registered 3D image representing the bone in the position of interest. There exist various techniques to register 3D and 2D images, and any of them may be used in the present invention. One may refer to [Hamadeh 1998] and [Hamadeh 1997] for a description of two registration methods. Other well-known methods of 3D/2D registration use a maximization of a similarity score between the projections of the 3D volume and the 2D projection, using cross correlation coefficient, entropy, or mutual information for example. It is to be noted that, contrary to the method of EP 3 398 551, these registration methods do not involve any segmentation of the images. The registration may be initialized using a bounding box drawn on either the 3D or the 2D image, the bounding box including at least a part of the bone.

In step 500, the surgical procedure is planned on the registered 3D image. Since the 3D image has been registered on the preoperative 2D X-ray image(s), the planning takes into account the position of interest. For example, hip surgery can be planned in a virtually standing patient, and in three dimensions.

According to an embodiment, the planning may have been done on the preoperative 2D X-ray images (step 101) and imported in the surgical system with the 2D X-ray images. In this case, step 500 comprises registering the 3D image with said preoperative planning.

In step 600, an optimal position of the surgical instrument to implement the planning defined in step 500 is determined.

For example, in the case of hip surgery, the optimal orientation of a prosthesis cup in inclination and anteversion is determined in a coordinate system of a patient standing, with values of angles that are meaningful.

In case of spine surgery, the planning of a deformity correction using screws and rods is performed for a standing reference position of the patient, and the relative desired positions and orientations can be defined vertebra per vertebra, once the 3D image area around each vertebra has been registered with the 2D X-ray image that include corrections. And the intra-operative correction of the whole spine can be compared in three dimensions with the planned correction. If only one lateral X-ray image is used pre-operatively, the spine correction is planned in said lateral X-ray image, on the basis of a standing position, in order to restore a convenient balance of the spine that falls within known values and references, registration is then performed for each vertebra by matching the 3D local volume around a vertebra and its projection. During surgery, several vertebrae are equipped with trackers, and it is now possible to compare the real sagittal balance of the spine with the desired balance before the rods are fully fixed and to correct accordingly if necessary.

In step 700, the surgical procedure is launched using a navigation device and/or a robotic device.

At this stage, the registration phantom is no longer required. Thus, if the above described modular device is used, the registration phantom may be detached from the base of the modular device and the localization element is attached to the base using the reproducible fixation to form the bone tracker. In case the localization element is permanently attached to the base, the localization element is present during all the protocol, including the previous steps.

Since the localization element has known position and fixation relative to the base, the computer implements an algorithm to register the above-mentioned 3D image with the coordinate system of the bone tracker.

In the case of optical tracking, a localization camera is installed in the vicinity of the patient such that the bone tracker is in the field of view of the camera.

A surgical instrument equipped with an instrument tracker is introduced in the operating field in order to carry out the surgical intervention. The instrument tracker is also in the field of view of the localization camera, such that the position of the instrument is known at each time.

With a navigation device, the user is provided with the registered 3D image onto which the planning has been done. The positions of the instrument tracker and bone tracker may be localized with respect to the registered 3D image. The user may then use the displayed image and planning to position the surgical instrument in an optimal way.

With a robotic device, the robot trajectory allowing implementing the planned procedure is computed and then executed.

Figure 5:
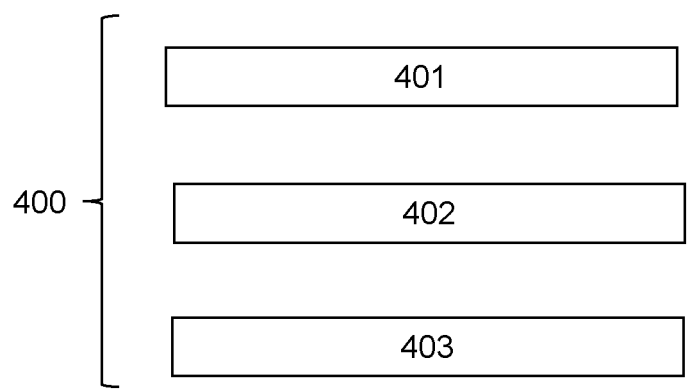
FIG. 5 represents a part of the flow chart of the method according to a second embodiment of the invention.

FIG. 5 illustrates an embodiment of the 2D/3D registration step 400, which may be implemented in case at least two bones are to be operated during the surgical intervention. In this case, each of said bones is equipped with a bone tracker.

Since the intraoperative 3D image is usually small, it may not include the whole set of bones. However, this is not detrimental to the method, provided that the 3D image includes at least the bone regions that are of interest for the surgical intervention. For example, for an intervention on a joint, said regions of interest may be the bone parts forming the joint (e.g. the acetabulum and the femoral head for a hip joint). For spine surgery, said regions of interest may be a few vertebrae that are equipped with a bone tracker. In the latter case, several intraoperative 3D images may be acquired and registered together to constitute a whole spine, with multiple trackers attached to several vertebrae.

In contrast, the preoperative 2D X-ray images are usually of a size sufficient to include the whole set of bones.

The 2D/3D registration will thus be done only in the regions of interest.

To that end, according to an embodiment, step 400 may comprise the following sub-steps.

In step 401, a bounding box is drawn on the preoperative 2D X-ray image(s) so as to encompass the region of interest. As mentioned above, in the case of a joint, a bounding box is drawn around the region of interest of each bone. In the case of spine, each vertebra equipped with a tracker forms a region of interest and a bounding box is drawn around each of said vertebrae. The bounding box is an advantageous tool for initializing the registration. Preferably, the shape of the bounding box is not necessarily a parallelepiped and it is as close as possible to the shape of the region of interest, in order to improve the convergence and increase the accuracy and reliability of the registration. The bounding box may be drawn manually by the user. Alternatively, the bounding box may be automatically drawn by the computer, and may be interactively adjusted by the user. However, such a bounding box does not involve any accurate segmentation of the bone.

In step 402, each region of interest defined by a respective bounding box is registered with the corresponding region of the intraoperative 3D image.

In step 403, an integrated 3D image is computed from the registered regions.

According to an alternative embodiment of step 400, the registration may not be initialized based on the preoperative 2D X-ray image(s) as described above, but on the intraoperative 3D image(s).

In this case, in step 401, a bounding box is drawn on the intraoperative 3D image(s) so as to encompass the regions of interest. As mentioned above, in the case of a joint, a bounding box is drawn around the region of interest of each bone. In the case of spine, each vertebra equipped with a tracker forms a region of interest and a bounding box is drawn around each of said vertebrae. The bounding box is an advantageous tool for initializing the registration. Preferably, the shape of the bounding box is as close as possible to the shape of the region of interest, in order to improve the convergence and increase the accuracy and reliability of the registration. The bounding box may be drawn manually by the user. Alternatively, the bounding box may be automatically drawn by the computer, and may be interactively adjusted by the user. However, such a bounding box does not involve any segmentation of the bone.

In step 402, each region of interest defined by a respective bounding box is registered with the corresponding region of the preoperative 2D X-ray image(s).

In step 403, an integrated 3D image is computed from the registered regions.

The planning of step 500 is then made on the integrated 3D image computed in step 403.

In these embodiments, the registration and the planning may thus not be carried out on the whole set of bones, but only locally in the determined regions of interest.

EXAMPLES

Hip Surgery

One application of the invention may be hip surgery, e.g. total hip arthroplasty, which is intended to implant an acetabular cup into the pelvis and a femoral prosthesis into the femur.

When planning the position and orientation of the prosthetic components, it is useful to take into the pelvis tilt, in order to prevent any malfunction of the hip joint.

To that end, in accordance with an embodiment of the invention, at least one preoperative 2D X-ray image of the hip joint is received.

Figure 6:
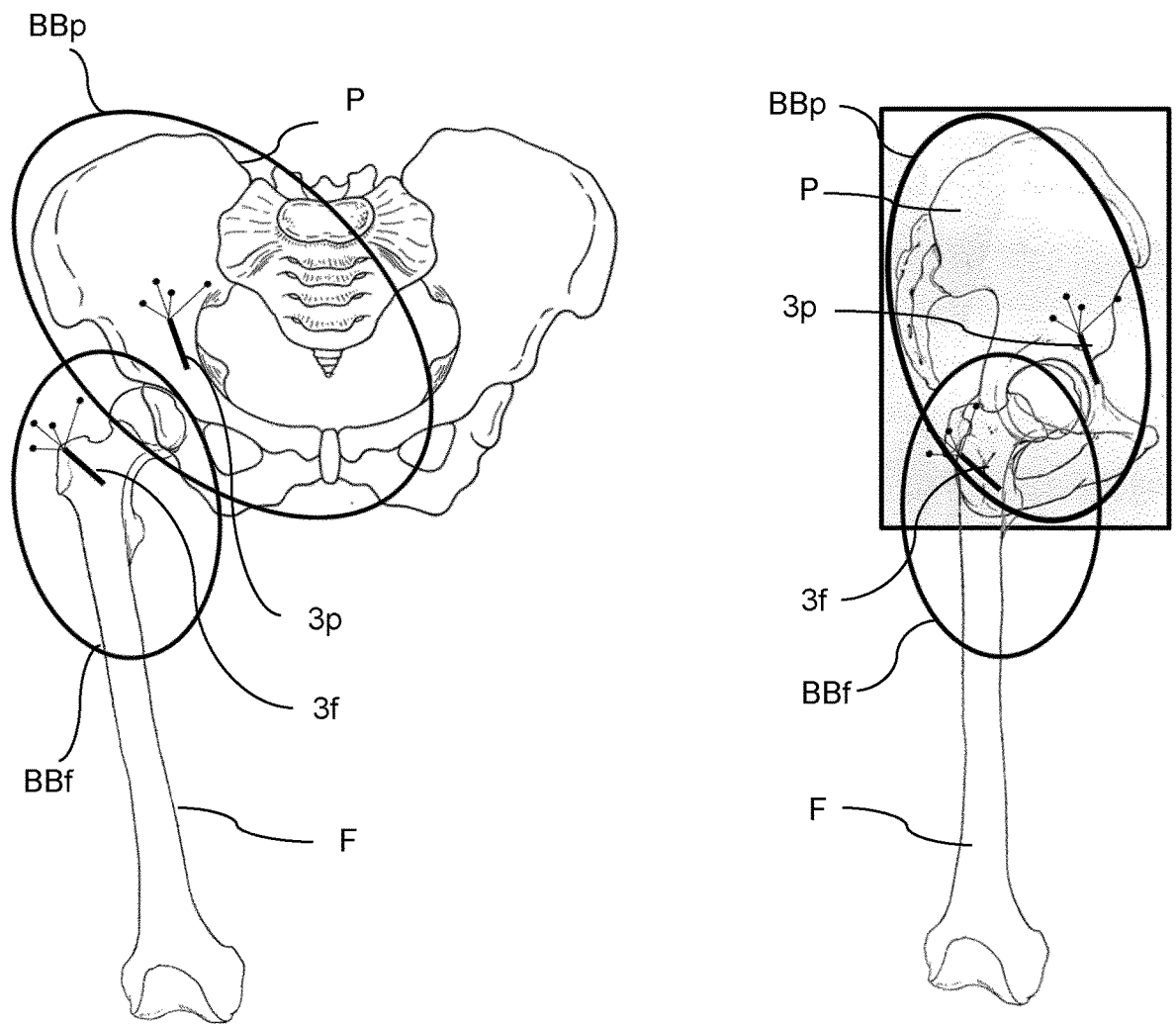
FIG. 6 schematically represents 2D pre-operative images of a patient's hip in frontal (left) and lateral (right) views.

FIG. 6 schematically represents preoperative 2D X-ray images of a patient's hip joint in frontal (left) and lateral (right) views.

In view of the intraoperative step, the patient is equipped with two bone trackers $3f$, $3p$, one rigidly connected to the femur and another one rigidly connected to the pelvis. Those trackers are represented in FIG. 6 in a symbolic manner for better understanding of the following method but they are not present during the acquisition of the pre-operative images.

The 3D image acquired intraoperatively is usually smaller than the preoperative 2D X-ray image but it must include at least the femoral head and the acetabulum.

The registration of the intraoperative 3D image and the preoperative 2D X-ray image may be made as follows.

A bounding box BBF is drawn around the femoral head in the preoperative 2D X-ray image.

Another bounding box BBp is drawn around the acetabulum in said preoperative 2D X-ray image.

Although the bounding boxes are schematically illustrated in FIG. 6 with oval shapes, it is to be noted that the bounding boxes may have a different shape. In particular, each bounding box may preferably have a shape that fits closely the shape of the region of interest of the corresponding bone. From a few landmarks such as a circle defining the hip sphere and a rough orientation of the acetabulum, it is possible to define automatically well adjusted bounding boxes.

Both regions of interest defined by a respective bounding box in the preoperative 2D X-ray image is registered with the corresponding region of the intraoperative 3D image.

The system thus computes a 3D integrated image from the registered regions.

The user may thus plan the position of the prosthetic components on said integrated 3D image. More precisely, the planning provides an optimal position of the acetabular cup relative to the tracker attached to the pelvis, and an optimal position of the femoral prosthesis relative to the tracker attached to the femur.

Spine Surgery

Figure 7:
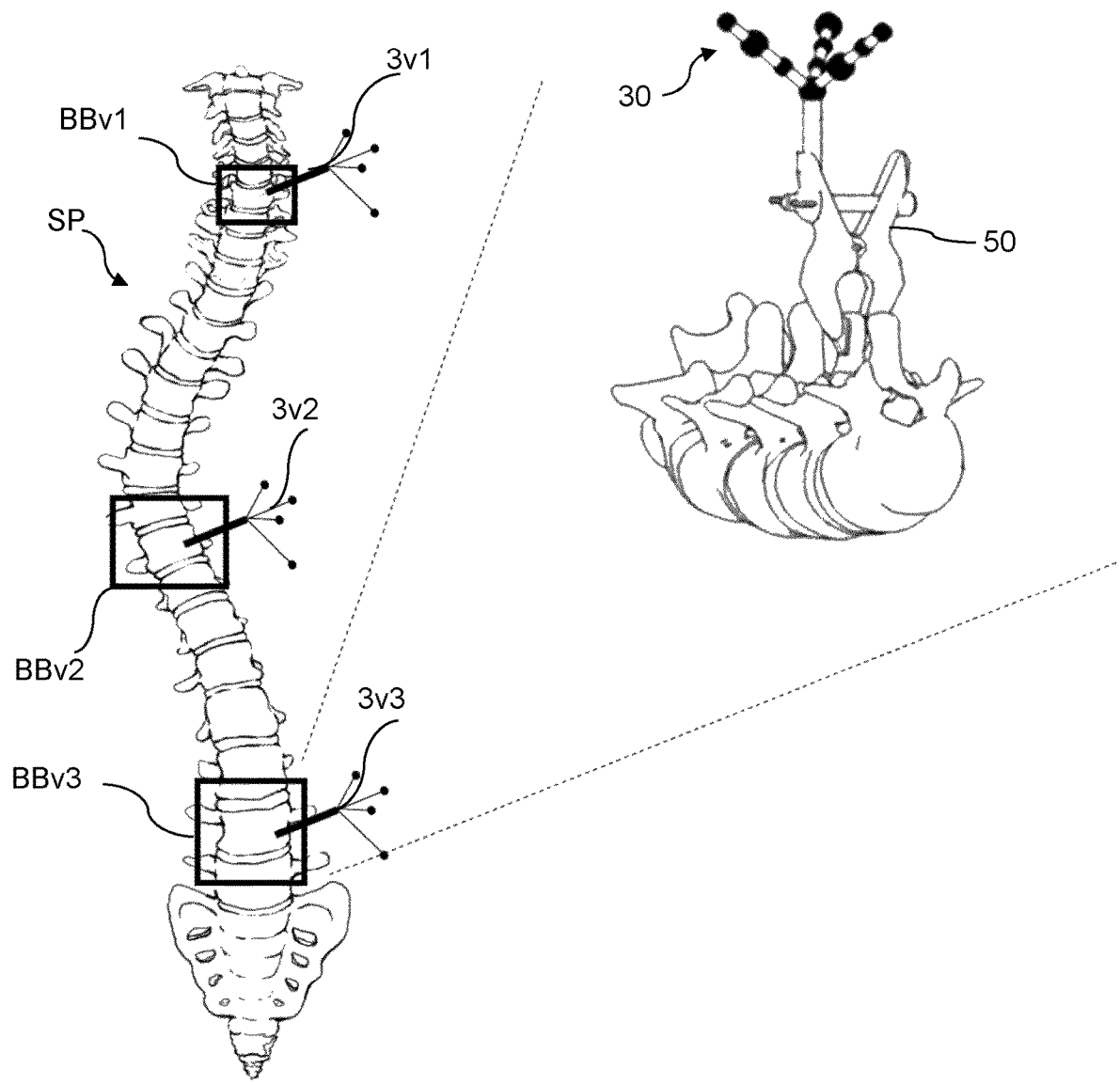
FIG. 7 schematically represents a part of a patient's spine (right) along with a 2D pre-operative image of the patient's spine (left).

FIG. 7 schematically represents a part of a patient's spine along with a 2D pre-operative image of the patient's spine. As can be seen in the right part of the figure, not all vertebrae are equipped with a bone tracker for the surgical intervention. Only a few vertebrae may be equipped by a tracker 3v1, 3v2, 3V3 attached to a respective vertebra using an attachment device 50 clamped on the vertebra. Patient trackers are represented in FIG. 7 in a symbolic manner for better understanding of the following method but they are not present during the acquisition of the pre-operative images.

The preoperative 2D X-ray image is sufficiently large to encompass the whole spine SP. Thus, all the vertebrae intended to be equipped with a bone tracker are visible in the preoperative 2D X-ray image.

The 3D image acquired intraoperatively is usually smaller than the preoperative 2D X-ray image and generally does not encompass the whole spine. Instead, a 3D preoperative image may be acquired for each vertebra equipped with a bone tracker, or for a set of such vertebrae.

The registration of the intraoperative 3D images and the preoperative 2D X-ray image may be made as follows.

A bounding box BBv1, BBv2, BBv3 is drawn in the preoperative 2D X-ray image around each vertebra equipped with a bone tracker.

Although the bounding boxes are schematically illustrated in FIG. 7 with square shapes, it is to be noted that the bounding boxes may have a different shape. In particular, each bounding box may preferably have a shape that fits closely the shape of the vertebra.

Each region of interest defined by a respective bounding box in the preoperative 2D X-ray image is registered with the corresponding intraoperative 3D image or region of the intraoperative 3D image. The bounding boxes allow efficiently initializing the registration by providing a correspondence between the vertebrae in the 2D and 3D images.

The system thus computes a 3D integrated image from the registered regions.

The user may thus plan an optimal position of a surgical correction on said integrated 3D image, including also screw and rods positions. The planning may define a position of a tracker attached to a vertebra relative to at least one tracker attached to another vertebra. In this respect, a bone tracker may be considered as a surgical instrument to be optimally positioned with respect to another bone tracker.

Of course, the invention is not limited to the above applications but may be used for any surgical intervention involving at least one bone, preferably when it is desired to take into account a position of interest of the patient when planning the intervention.

In a preferred embodiment, the position of interest is the standing position of the patient. In another preferred embodiment, the position of interest is the sitting position of the patient. In the case of shoulder surgery, the position of interest may be the extreme motion of the humerus with respect to the scapula, before surgery.

In another embodiment, the intraoperative 3D images obtained during surgery can be registered with post-operative 2D X-ray images. This method offers a complete chain to compare surgical planning performed on standing 2D X-ray images and post-operative results obtained on other standing 2D X-ray images. This method can be applied for other positions of interest.

REFERENCES

EP 3 398 551
WO 2017/064290
[Hamadeh 1998] Ali Hamadeh, Stéphane Lavallée, Philippe Cinquin, Automated 3-Dimensional Computed Tomographic and Fluoroscopic Image Registration, Computer Aided Surgery, 3:11-19 (1998)
[Hamadeh 1997]Ali Hamadeh, Philippe Cinquin, Kinematic Study of Lumbar Spine Using Functional Radiographies and 3D/2D registration, In: Troccaz J., Grimson E., Mösges R. (eds) CVRMed-MRCAS'97. CVRMed 1997, MRCAS 1997. Lecture Notes in Computer Science, vol 1205. Springer, Berlin, Heidelberg

The invention claimed is:

1. A method for determining an optimal position of a surgical instrument relative to a tracker attached to a patient's bone using a cone beam computed tomography (CBCT) imaging system and a computer, the method comprising the following steps:
   (a) receiving at least one preoperative 2D X-ray image of the bone while the patient is in a posture of interest, the posture of interest being a posture that has an impact on a configuration of the bone and on interaction of the bone with other anatomical structures of the patient;
   (b) acquiring an intraoperative 3D CBCT medical image of the bone by the cone beam computed tomography (CBCT) imaging system while the patient is in an operative posture, in which a position and an orientation of the bone relative to another anatomical structure of the patient is different from the one in the posture of interest, the intraoperative 3D CBCT medical image being registered with the coordinate system of the bone tracker;
   (c) registering with the computer the intraoperative 3D CBCT medical image onto the at least one preoperative 2D X-ray image, so as to obtain a registered 3D CBCT medical image representing the bone in the posture of interest;
   (d) planning with the computer a surgical procedure on the registered 3D medical image taking into account said posture of interest;
   (e) determining with the computer an optimal position of the surgical instrument relative to the patient's bone tracker for implementing said planned surgical procedure.

2. The method of claim 1, wherein the posture of interest is a standing position of the patient.

3. The method of claim 1, wherein the operative posture is a lying position of the patient.

4. The method of claim 1, wherein the at least one preoperative 2D X-ray image received in step (a) is geometrically calibrated, the features of the geometric projection of an imaged object onto the image plane being known.

5. The method of claim 1, wherein at least two preoperative 2D X-ray images are received in step (a) and said at least two preoperative 2D X-ray images are geometrically calibrated, the features of the geometric projection of an imaged object onto each image plane being known, and registered with each other.

6. The method of claim 1, wherein step (d) comprises a step of importing a preoperative planning based on the at least one preoperative 2D X-ray image received in step (a).

7. The method of claim 1, further comprising acquiring at least two intraoperative 2D X-ray images on which at least one anatomical landmark of the patient is visible and determining a position of said anatomical landmark of the patient from said at least two intraoperative 2D X-ray images.

8. The method of claim 1, wherein step (e) uses a preoperative planning based on the at least one preoperative 2D X-ray image acquired in step (a).

9. The method of claim 1, further comprising receiving at least one postoperative 2D X-ray image of the bone(s) while the patient is in the posture of interest and registering the intraoperative 3D CBCT medical image with said postoperative 2D X-ray image.

10. A method for determining an optimal position of a surgical instrument relative to trackers respectively attached to at least two patient's bones using a cone beam computed tomography (CBCT) imaging system and a computer, the method comprising the following steps:
(a) receiving at least one preoperative 2D X-ray image of the at least two bones while the patient is in a posture of interest;
(b) acquiring at least one intraoperative 3D CBCT medical image of each bone by the cone beam computed tomography (CBCT) imaging system while the patient is in an operative posture, in which a position and an orientation of each bone relative to another anatomical structure of the patient is different from the one in the posture of interest, each of the at least one intraoperative 3D CBCT medical image being registered with the coordinate system of each bone tracker;
(c) performing one of steps c1) and c2) with the computer:
(c1) determining a region around each bone in the at least one preoperative 2D X-ray image and registering said at least one region onto the intraoperative 3D CBCT medical image, so as to obtain a registered region around each bone in the intraoperative 3D CBCT medical image representing each bone in the posture of interest, respectively;
(c2) determining a region around each bone in the intraoperative 3D CBCT medical image and registering said region onto the at least one preoperative 2D X-ray image, so as to obtain a registered region around each bone in the at least one 2D preoperative X-ray image representing each bone in the posture of interest, respectively;
(c3) computing with the computer an integrated 3D medical image from the registered regions determined in step (c1) or (c2);
(d) planning with the computer a surgical procedure on the integrated 3D medical image taking into account said posture of interest;
(e) determining with the computer an optimal position of the surgical instrument relative to the patient's bone trackers for implementing said planned surgical procedure.

11. The method of claim 10, wherein the posture of interest is a standing position of the patient.

12. The method of claim 10, wherein the operative posture is a lying position of the patient.

13. The method of claim 10, wherein the at least one preoperative 2D X-ray image received in step (a) is geometrically calibrated, the features of the geometric projection of an imaged object onto the image plane being known.

14. The method of claim 10, wherein at least two preoperative 2D X-ray images are received in step (a) and said images are geometrically calibrated, the features of the geometric projection of an imaged object onto each image plane being known, and registered with each other.

15. The method of claim 10, wherein step (d) comprises a step of importing a preoperative planning based on the at least one preoperative 2D X-ray image received in step (a).

16. The method of claim 10, further comprising acquiring at least two intraoperative 2D X-ray images on which at least one anatomical landmark of the patient is visible and determining a position of said anatomical landmark of the patient from said at least two intraoperative 2D X-ray images.

17. The method of claim 10, wherein step (e) uses a preoperative planning based on the at least one preoperative 2D X-ray image acquired in step (a).

18. The method of claim 10, further comprising receiving at least one postoperative 2D X-ray image of the bone(s) while the patient is in the posture of interest and registering the intraoperative 3D CBCT medical image with said postoperative 2D X-ray image.

19. A system for determining an optimal position of a surgical instrument relative to at least one tracker attached to a respective patient's bone, comprising:
a medical imaging system configured to acquire at least one cone beam computed tomography (CBCT) intraoperative image of the patient;
a localization device;
a computer configured to receive images from the medical imaging system and localization data from the localization device and to implement at least one of the following methods:
(A) a first method comprising:
(a) receiving at least one preoperative 2D X-ray image of the bone while the patient is in a posture of interest;
(b) acquiring an intraoperative 3D CBCT medical image of the bone by the cone beam computed tomography (CBCT) imaging system while the patient is in an operative posture in which a position and an orientation of the bone relative to another anatomical structure of the patient is different from the position posture of interest, the intraoperative 3D CBCT image being registered with the coordinate system of the bone tracker;
(c) registering the intraoperative 3D CBCT medical image onto the at least one preoperative 2D X-ray image, so as to obtain a registered 3D image representing the bone in the posture of interest;
(d) planning a surgical procedure on the registered 3D medical image taking into account said posture of interest;
(e) determining an optimal position of the surgical instrument relative to the patient's bone tracker for implementing said planned surgical procedure; and
(B) a second method comprising:
(a) receiving at least one preoperative 2D X-ray image of the at least two bones while the patient is in a posture of interest;
(b) acquiring at least one intraoperative 3D CBCT medical image of each bone by the cone beam computed tomography (CBCT) imaging system while the patient is in an operative posture in which a position and an orientation of each bone relative to another anatomical structure of the patient is different from the posture of interest, each intraoperative 3D CBCT medical image being registered with the coordinate system of each bone tracker;
(c) performing one of steps c1) and c2):
(c1) determining a region around each bone in the at least one preoperative 2D X-ray image and registering said at least one region onto the intraoperative 3D CBCT medical image, so as to obtain a registered region around each bone in the intraoperative 3D CBCT medical image representing each bone in the position posture of interest, respectively;

(c2) determining a region around each bone in the intraoperative 3D CBCT medical image and registering said region onto the at least one preoperative 2D X-ray image, so as to obtain a registered region around each bone in the at least one 2D preoperative X-ray image representing each bone in the posture of interest, respectively;

(c3) computing an integrated 3D medical image from the registered regions determined in step (c1) or (c2);

(d) planning a surgical procedure on the integrated 3D medical image taking into account said posture of interest;

(e) determining an optimal position of the surgical instrument relative to the patient's bone trackers for implementing said planned surgical procedure.

20. The system of claim 19, further comprising a monitor display coupled to the computer and configured to display the registered 3D image along with the planning.

21. The system of claim 19, further comprising a robot configured to position a tool and/or prepare the bone to receive an implant based on the optimal position of the surgical instrument relative to the patient's bone tracker for implementing the planned surgical procedure.

* * * * *